(12) United States Patent
Furnish et al.

(10) Patent No.: US 9,615,824 B2
(45) Date of Patent: *Apr. 11, 2017

(54) HANDLE ASSEMBLY FOR ENDOSCOPIC SUTURING DEVICE

(71) Applicant: COVIDIEN LP, Mansfield, MA (US)

(72) Inventors: Greg Furnish, Louisville, KY (US);
Eric Bielefeld, New Albany, IN (US);
Edwin Bon, Floyds Knobs, IN (US);
Eric Taylor, East Hampton, CT (US);
Peter Hathaway, Lebanon, CT (US);
Matthew Chowaniec, Middletown, CT (US)

(73) Assignee: Covidien LP, Mansfield, MA (US)

( * ) Notice: Subject to any disclaimer, the term of this patent is extended or adjusted under 35 U.S.C. 154(b) by 865 days.

This patent is subject to a terminal disclaimer.

(21) Appl. No.: 13/938,345

(22) Filed: Jul. 10, 2013

(65) Prior Publication Data

US 2013/0310848 A1    Nov. 21, 2013

Related U.S. Application Data

(63) Continuation of application No. 12/896,324, filed on Oct. 1, 2010, now Pat. No. 8,490,713.

(Continued)

(51) Int. Cl.
*A61B 17/04* (2006.01)
*A61B 17/062* (2006.01)
(Continued)

(52) U.S. Cl.
CPC ...... *A61B 17/0469* (2013.01); *A61B 17/0625* (2013.01); *A61B 2017/00327* (2013.01);
(Continued)

(58) Field of Classification Search
CPC .... A61B 2017/2946; A61B 2017/2923; A61B 17/2943; A61B 17/2909
See application file for complete search history.

(56) References Cited

U.S. PATENT DOCUMENTS 1,822,330 A    9/1931   Ainslie
2,327,353 A    8/1943   Karle
(Continued)

FOREIGN PATENT DOCUMENTS

DE    44 23 881 C1    10/1995
EP    0 592 244 A2    4/1994
(Continued)

OTHER PUBLICATIONS

European Search Report from EP 07 83 9340 dated Dec. 2, 2013 (8 pages).

(Continued)

*Primary Examiner* — Andrew M Tecco

(57) ABSTRACT

A handle assembly for operating an articulatable surgical instrument is provided and includes a housing; an actuation shaft translatably and rotatably supported in the housing; a first trigger supported on the housing and connected to the actuation shaft, the first trigger being configured to translate the actuation shaft to operate a first function of the surgical instrument; a second trigger supported on the housing and connected to the actuation shaft, the second trigger being configured to rotate the actuation shaft to operate a second function of the surgical instrument; and a second-trigger release supported in the housing, the second-trigger release having a first position blocking actuation of the second trigger and a second position permitting actuation of the second trigger, where the second-trigger release is actuated from the first position to the second position upon and complete actuation of the first trigger.

19 Claims, 14 Drawing Sheets

Related U.S. Application Data

(60) Provisional application No. 61/249,073, filed on Oct. 6, 2009.

(51) Int. Cl.
  *A61B 17/00* (2006.01)
  *A61B 17/06* (2006.01)
  *A61B 17/29* (2006.01)
  *A61B 90/00* (2016.01)

(52) U.S. Cl.
  CPC ........... *A61B 2017/0609* (2013.01); *A61B 2017/2923* (2013.01); *A61B 2017/2925* (2013.01); *A61B 2090/0811* (2016.02)

(56) References Cited

U.S. PATENT DOCUMENTS

| | | |
|---|---|---|
| 3,073,311 A | 1/1963 | Tibbs et al. |
| 3,123,077 A | 3/1964 | Alcamo |
| 4,236,470 A | 12/1980 | Stenson |
| 4,890,615 A | 1/1990 | Caspari et al. |
| 4,923,461 A | 5/1990 | Caspari et al. |
| 4,935,027 A | 6/1990 | Yoon |
| 5,037,433 A | 8/1991 | Wilk et al. |
| 5,042,707 A | 8/1991 | Taheri |
| 5,080,663 A | 1/1992 | Mills et al. |
| 5,100,421 A | 3/1992 | Christoudias |
| 5,100,430 A | 3/1992 | Aveillanet et al. |
| 5,209,747 A | 5/1993 | Knoepfler |
| 5,271,543 A | 12/1993 | Grant et al. |
| 5,300,082 A | 4/1994 | Sharpe et al. |
| 5,308,353 A | 5/1994 | Beurrier |
| 5,314,445 A | 5/1994 | Heidmueller nee Degwitz et al. |
| 5,314,446 A | 5/1994 | Hunter et al. |
| 5,330,502 A | 7/1994 | Hassler et al. |
| 5,336,229 A | 8/1994 | Noda |
| 5,350,391 A | 9/1994 | Iacovelli |
| 5,358,498 A | 10/1994 | Shave |
| 5,374,277 A | 12/1994 | Hassler |
| 5,387,221 A | 2/1995 | Bisgaard |
| 5,389,103 A | 2/1995 | Melzer et al. |
| 5,391,176 A | 2/1995 | de la Torre |
| 5,403,342 A | 4/1995 | Tovey et al. |
| 5,405,352 A | 4/1995 | Weston |
| 5,439,478 A | 8/1995 | Palmer |
| 5,454,823 A | 10/1995 | Richardson et al. |
| 5,454,827 A | 10/1995 | Aust et al. |
| 5,472,446 A | 12/1995 | de la Torre |
| 5,478,344 A | 12/1995 | Stone et al. |
| 5,480,406 A | 1/1996 | Nolan et al. |
| 5,496,334 A | 3/1996 | Klundt et al. |
| 5,527,323 A | 6/1996 | Jervis et al. |
| 5,540,703 A | 7/1996 | Barker, Jr. et al. |
| 5,540,706 A | 7/1996 | Aust et al. |
| 5,549,617 A | 8/1996 | Green et al. |
| 5,549,637 A | 8/1996 | Crainich |
| 5,562,686 A | 10/1996 | Sauer et al. |
| 5,564,615 A | 10/1996 | Bishop et al. |
| 5,571,090 A | 11/1996 | Sherts |
| 5,573,286 A | 11/1996 | Rogozinski |
| 5,575,799 A | 11/1996 | Bolanos et al. |
| 5,582,617 A | 12/1996 | Klieman et al. |
| 5,591,181 A | 1/1997 | Stone et al. |
| 5,601,224 A | 2/1997 | Bishop et al. |
| 5,620,415 A | 4/1997 | Lucey et al. |
| 5,628,756 A | 5/1997 | Barker, Jr. et al. |
| 5,630,825 A | 5/1997 | de la Torre et al. |
| 5,632,751 A | 5/1997 | Piraka |
| 5,643,293 A | 7/1997 | Kogasaka et al. |
| 5,643,294 A | 7/1997 | Tovey et al. |
| 5,662,666 A | 9/1997 | Onuki et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,690,653 A | 11/1997 | Richardson et al. |
| 5,702,408 A | 12/1997 | Wales et al. |
| 5,715,942 A | 2/1998 | Li et al. |
| 5,728,107 A | 3/1998 | Zlock et al. |
| 5,728,109 A | 3/1998 | Schulze et al. |
| 5,728,113 A | 3/1998 | Sherts |
| 5,730,747 A | 3/1998 | Ek et al. |
| 5,735,874 A * | 4/1998 | Measamer ......... A61B 17/2909 606/208 |
| 5,746,751 A | 5/1998 | Sherts |
| 5,749,898 A | 5/1998 | Schulze et al. |
| 5,752,973 A | 5/1998 | Kieturakis |
| 5,755,729 A | 5/1998 | de la Torre et al. |
| 5,759,188 A | 6/1998 | Yoon |
| 5,766,196 A | 6/1998 | Griffiths |
| 5,779,646 A | 7/1998 | Koblish et al. |
| 5,792,153 A | 8/1998 | Swain et al. |
| 5,792,165 A | 8/1998 | Klieman et al. |
| 5,797,537 A | 8/1998 | Oberlin et al. |
| 5,797,927 A | 8/1998 | Yoon |
| 5,797,928 A | 8/1998 | Kogasaka |
| 5,814,054 A | 9/1998 | Kortenbach et al. |
| 5,814,069 A | 9/1998 | Schulze et al. |
| 5,817,119 A | 10/1998 | Klieman et al. |
| 5,827,323 A | 10/1998 | Klieman et al. |
| 5,865,836 A | 2/1999 | Miller |
| 5,871,488 A | 2/1999 | Tovey et al. |
| 5,876,412 A | 3/1999 | Piraka |
| 5,893,592 A | 4/1999 | Schulze et al. |
| 5,897,563 A | 4/1999 | Yoon et al. |
| 5,906,630 A | 5/1999 | Anderhub et al. |
| 5,908,428 A | 6/1999 | Scirica et al. |
| 5,911,727 A | 6/1999 | Taylor |
| 5,928,136 A | 7/1999 | Barry |
| 5,931,855 A | 8/1999 | Buncke |
| 5,938,668 A | 8/1999 | Scirica et al. |
| 5,941,430 A | 8/1999 | Kuwabara |
| 5,947,982 A | 9/1999 | Duran |
| 5,954,731 A | 9/1999 | Yoon |
| 5,954,733 A | 9/1999 | Yoon |
| 5,957,937 A | 9/1999 | Yoon |
| 5,980,538 A | 11/1999 | Fuchs et al. |
| 5,984,932 A | 11/1999 | Yoon |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,017,358 A | 1/2000 | Yoon et al. |
| 6,027,522 A | 2/2000 | Palmer |
| 6,051,006 A | 4/2000 | Shluzas et al. |
| 6,071,289 A | 6/2000 | Stefanchik et al. |
| 6,077,287 A | 6/2000 | Taylor et al. |
| 6,080,180 A | 6/2000 | Yoon |
| 6,086,601 A | 7/2000 | Yoon |
| 6,119,913 A | 9/2000 | Adams et al. |
| 6,126,665 A | 10/2000 | Yoon |
| 6,126,666 A | 10/2000 | Trapp et al. |
| 6,139,563 A | 10/2000 | Cosgrove, III et al. |
| 6,143,004 A | 11/2000 | Davis et al. |
| 6,143,005 A | 11/2000 | Yoon et al. |
| 6,171,316 B1 | 1/2001 | Kovac et al. |
| 6,206,893 B1 | 3/2001 | Klein et al. |
| 6,214,028 B1 | 4/2001 | Yoon et al. |
| 6,223,100 B1 | 4/2001 | Green |
| 6,224,614 B1 | 5/2001 | Yoon |
| 6,261,307 B1 | 7/2001 | Yoon et al. |
| 6,270,508 B1 | 8/2001 | Klieman et al. |
| 6,277,132 B1 | 8/2001 | Brhel |
| 6,319,262 B1 | 11/2001 | Bates et al. |
| 6,332,889 B1 | 12/2001 | Sancoff et al. |
| 6,346,111 B1 | 2/2002 | Gordon et al. |
| 6,358,259 B1 | 3/2002 | Swain et al. |
| 6,494,888 B1 | 12/2002 | Laufer et al. |
| 6,506,196 B1 | 1/2003 | Laufer |
| 6,517,539 B1 | 2/2003 | Smith et al. |
| 6,533,796 B1 | 3/2003 | Sauer et al. |
| 6,569,105 B1 | 5/2003 | Kortenbach et al. |
| 6,582,450 B2 | 6/2003 | Ouchi |

(56) References Cited

U.S. PATENT DOCUMENTS

| | | |
|---|---|---|
| 6,596,015 B1 | 7/2003 | Pitt et al. |
| 6,599,310 B2 | 7/2003 | Leung et al. |
| 6,638,287 B2 | 10/2003 | Danitz et al. |
| 6,663,639 B1 | 12/2003 | Laufer et al. |
| 6,663,641 B1 | 12/2003 | Kovac et al. |
| 6,666,854 B1 | 12/2003 | Lange |
| 6,676,676 B2 | 1/2004 | Danitz et al. |
| 6,719,764 B1 | 4/2004 | Gellman et al. |
| 6,719,765 B2 | 4/2004 | Bonutti |
| 6,743,239 B1 | 6/2004 | Kuehn et al. |
| 6,743,240 B2 | 6/2004 | Smith et al. |
| 6,755,843 B2 | 6/2004 | Chung et al. |
| 6,773,441 B1 | 8/2004 | Laufer et al. |
| 6,786,913 B1 | 9/2004 | Sancoff et al. |
| 6,821,285 B2 | 11/2004 | Laufer et al. |
| 6,835,200 B2 | 12/2004 | Laufer et al. |
| 6,889,116 B2 | 5/2005 | Jinno |
| 6,936,054 B2 | 8/2005 | Chu |
| 6,936,061 B2 | 8/2005 | Sasaki |
| 6,955,643 B2 | 10/2005 | Gellman et al. |
| 6,972,017 B2 | 12/2005 | Smith et al. |
| 6,981,628 B2 | 1/2006 | Wales |
| 6,991,635 B2 | 1/2006 | Takamoto et al. |
| 6,997,931 B2 | 2/2006 | Sauer et al. |
| 7,011,668 B2 | 3/2006 | Sancoff et al. |
| 7,037,315 B2 | 5/2006 | Sancoff et al. |
| 7,041,111 B2 | 5/2006 | Chu |
| 7,052,489 B2 | 5/2006 | Griego et al. |
| RE39,152 E | 6/2006 | Aust et al. |
| 7,063,710 B2 | 6/2006 | Takamoto et al. |
| 7,063,715 B2 | 6/2006 | Onuki et al. |
| 7,107,124 B2 | 9/2006 | Green |
| 7,153,314 B2 | 12/2006 | Laufer et al. |
| 7,191,900 B2 | 3/2007 | Opie et al. |
| 7,192,437 B2 | 3/2007 | Shalaby |
| 7,211,093 B2 | 5/2007 | Sauer et al. |
| 7,218,972 B2 | 5/2007 | Rodriguez |
| 7,232,448 B2 | 6/2007 | Battles et al. |
| 7,244,260 B2 | 7/2007 | Koseki |
| 7,248,944 B2 | 7/2007 | Green |
| 7,364,061 B2 * | 4/2008 | Swayze ............ A61B 17/07207 227/175.1 |
| 7,431,189 B2 * | 10/2008 | Shelton, IV ......... A61B 17/068 227/176.1 |
| 7,468,068 B2 | 12/2008 | Kolster |
| 7,601,164 B2 | 10/2009 | Wu |
| 7,645,284 B2 | 1/2010 | Burbank et al. |
| 7,666,194 B2 | 2/2010 | Field et al. |
| 7,691,112 B2 | 4/2010 | Chanduszko et al. |
| 7,704,261 B2 | 4/2010 | Sakamoto et al. |
| 7,708,747 B2 | 5/2010 | Bjerken |
| 7,722,630 B1 | 5/2010 | Stone et al. |
| 7,731,726 B2 | 6/2010 | Belhe et al. |
| 7,736,372 B2 | 6/2010 | Reydel et al. |
| 7,758,597 B1 | 7/2010 | Tran et al. |
| 7,758,598 B2 | 7/2010 | Conlon et al. |
| 7,766,925 B2 | 8/2010 | Stokes et al. |
| 7,771,438 B2 | 8/2010 | Dreyfuss et al. |
| 7,776,059 B2 | 8/2010 | Craig |
| 7,776,066 B2 | 8/2010 | Onuki et al. |
| 7,780,701 B1 | 8/2010 | Meridew et al. |
| 7,784,612 B2 | 8/2010 | Kanda et al. |
| 7,798,325 B2 | 9/2010 | Wizemann et al. |
| 7,814,630 B2 | 10/2010 | Price et al. |
| 7,815,654 B2 | 10/2010 | Chu |
| 7,815,659 B2 | 10/2010 | Conlon et al. |
| 7,828,812 B2 | 11/2010 | Stokes et al. |
| 7,833,235 B2 | 11/2010 | Chu |
| 7,833,237 B2 | 11/2010 | Sauer |
| 7,837,696 B2 | 11/2010 | Modesitt et al. |
| 7,842,047 B2 | 11/2010 | Modesitt et al. |
| 7,842,048 B2 | 11/2010 | Ma |
| 7,846,170 B2 | 12/2010 | Modesitt et al. |
| 7,850,701 B2 | 12/2010 | Modesitt et al. |
| 7,883,517 B2 | 2/2011 | Pantages et al. |
| 7,883,519 B2 | 2/2011 | Oren et al. |
| 7,887,554 B2 | 2/2011 | Stokes et al. |
| 7,935,128 B2 | 5/2011 | Rioux et al. |
| 7,947,052 B2 | 5/2011 | Baxter, III et al. |
| 7,947,053 B2 | 5/2011 | McKay et al. |
| 7,951,157 B2 | 5/2011 | Gambale |
| 7,967,832 B2 | 6/2011 | Chu |
| 7,967,842 B2 | 6/2011 | Bakos |
| 7,972,344 B2 | 7/2011 | Murray et al. |
| 7,976,552 B2 | 7/2011 | Suzuki |
| 8,292,906 B2 | 10/2012 | Taylor et al. |
| 8,490,713 B2 * | 7/2013 | Furnish ............. A61B 17/0469 173/18 |
| 2002/0010480 A1 | 1/2002 | Sancoff et al. |
| 2002/0065526 A1 | 5/2002 | Oren et al. |
| 2002/0072702 A1 | 6/2002 | Quay |
| 2002/0128666 A1 | 9/2002 | Sancoff et al. |
| 2002/0173800 A1 | 11/2002 | Dreyfuss et al. |
| 2002/0198542 A1 | 12/2002 | Yamamoto et al. |
| 2003/0009195 A1 | 1/2003 | Field et al. |
| 2003/0014077 A1 | 1/2003 | Leung et al. |
| 2003/0045891 A1 | 3/2003 | Yamamoto et al. |
| 2003/0105475 A1 | 6/2003 | Sancoff et al. |
| 2003/0105476 A1 | 6/2003 | Sancoff et al. |
| 2003/0114863 A1 | 6/2003 | Field et al. |
| 2003/0116670 A1 | 6/2003 | Gentry |
| 2003/0171761 A1 | 9/2003 | Sancoff et al. |
| 2003/0233104 A1 | 12/2003 | Gellman et al. |
| 2004/0010245 A1 | 1/2004 | Cerier et al. |
| 2004/0060410 A1 | 4/2004 | Leung et al. |
| 2004/0068272 A1 | 4/2004 | Sauer et al. |
| 2004/0087976 A1 | 5/2004 | DeVries et al. |
| 2004/0092967 A1 | 5/2004 | Sancoff et al. |
| 2004/0181243 A1 | 9/2004 | Chu et al. |
| 2004/0193186 A1 | 9/2004 | Kortenbach et al. |
| 2004/0199184 A1 | 10/2004 | Topper et al. |
| 2005/0043747 A1 | 2/2005 | Field et al. |
| 2005/0085832 A1 | 4/2005 | Sancoff et al. |
| 2005/0096694 A1 | 5/2005 | Lee |
| 2005/0126876 A1 | 6/2005 | Simmons |
| 2005/0165419 A1 | 7/2005 | Sauer et al. |
| 2005/0256533 A1 | 11/2005 | Roth et al. |
| 2006/0025817 A1 | 2/2006 | Ortiz et al. |
| 2006/0036232 A1 | 2/2006 | Primavera et al. |
| 2006/0069396 A1 | 3/2006 | Meade et al. |
| 2006/0111209 A1 | 5/2006 | Hinman et al. |
| 2006/0111732 A1 | 5/2006 | Gibbens et al. |
| 2006/0235304 A1 | 10/2006 | Harhen et al. |
| 2006/0253126 A1 | 11/2006 | Bjerken et al. |
| 2006/0282093 A1 | 12/2006 | Shelton, IV et al. |
| 2007/0005110 A1 | 1/2007 | Collier et al. |
| 2007/0175953 A1 * | 8/2007 | Shelton, IV ...... A61B 17/07207 227/176.1 |
| 2008/0188868 A1 | 8/2008 | Weitzner et al. |
| 2008/0312688 A1 | 12/2008 | Nawrocki et al. |
| 2009/0259233 A1 | 10/2009 | Bogart et al. |
| 2010/0076260 A1 * | 3/2010 | Taylor ................ A61B 17/2909 600/104 |
| 2011/0082476 A1 * | 4/2011 | Furnish ............. A61B 17/0469 606/144 |

FOREIGN PATENT DOCUMENTS

| | | |
|---|---|---|
| EP | 0 647 431 A2 | 4/1995 |
| EP | 1 481 628 A1 | 12/2004 |
| EP | 1 915 957 A2 | 4/2008 |
| EP | 1 915 966 A1 | 4/2008 |
| EP | 2 044 890 A1 | 4/2009 |
| WO | WO 98/11814 A2 | 3/1998 |
| WO | WO 98/11829 A1 | 3/1998 |
| WO | WO 98/53745 A1 | 12/1998 |
| WO | WO 99/15090 A1 | 4/1999 |
| WO | WO 99/18859 A1 | 4/1999 |
| WO | WO 00/67834 A1 | 11/2000 |
| WO | WO 01/74254 A | 10/2001 |
| WO | WO 02/34147 A1 | 5/2002 |
| WO | WO 03/017850 A2 | 3/2003 |
| WO | 03028541 A2 | 4/2003 |

(56) References Cited

FOREIGN PATENT DOCUMENTS

| WO | WO 2006/061868 A | 6/2006 |
|---|---|---|
| WO | WO 2008/042423 A2 | 4/2008 |
| WO | WO 2008/045333 | 4/2008 |
| WO | WO 2008/045333 A | 4/2008 |
| WO | WO 2009/061504 | 5/2009 |
| WO | 2009/132284 A2 | 10/2009 |

OTHER PUBLICATIONS

European Search Report for EP 22 25 0290 dated Sep. 11, 2014.
Extended European Search Report for EP 07 83 9323 dated Sep. 4, 2014.
Extended European Search Report corresponding to EP 10 25 1738.0, completed Mar. 13, 2014 and mailed Mar. 20, 2014; (5 pp).
International Search Report for PCT/US2007/021506 mailed Apr. 16, 2008 (2 pgs.).
European Search Report for EP 07839357.6 date of completion Oct. 31, 2012 (10 pgs.).
European Search Report for EP 09251544.4 mailed Feb. 28, 2013 (18 pgs.).
European Search Report for EP12169361.8 mailed Aug. 6, 2012.
International Search Report for PCT/US07/021447 date of completion is Jan. 25, 2008 (2 pages).
International Search Report for PCT/US2007/021480 date of completion is Feb. 28, 2008 (2 pages).

* cited by examiner

HANDLE ASSEMBLY FOR ENDOSCOPIC SUTURING DEVICE

CROSS-REFERENCE TO RELATED APPLICATIONS

The present application is a Continuation application of U.S. patent application Ser. No. 12/896,324, filed on Oct. 1, 2010, which claims the benefit of and priority to U.S. Provisional Application Ser. No. 61/249,073, filed on Oct. 6, 2009, the entire content of which is hereby incorporated by reference.

BACKGROUND

Technical Field

The present disclosure relates to surgical handle assemblies and, more particularly, to handle assemblies for endoscopic suturing and/or stitching devices or the like.

Background

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and, therefore, the hospital and medical costs can be reduced as well.

One of the truly great advances in recent years to reduce the invasiveness of surgical procedures is endoscopic surgery. Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss. Heat and water loss are greatly reduced as a result of the smaller incisions.

In many surgical procedures, including those involved in endoscopic surgery, it is often necessary to suture bodily organs or tissue. The latter is especially challenging during endoscopic surgery because of the small openings through which the suturing of bodily organs or tissues must be accomplished.

In the past, suturing of bodily organs or tissue through endoscopic surgery was achieved through the use of a sharp metal suture needle which had attached at one of its ends a length of suture material. The surgeon would cause the suture needle to penetrate and pass through bodily tissue, pulling the suture material through the bodily tissue. Once the suture material was pulled through the bodily tissue, the surgeon proceeded to tie a knot in the suture material. The knotting of the suture material allowed the surgeon to adjust the tension on the suture material to accommodate the particular tissue being sutured and control approximation, occlusion, attachment or other conditions of the tissue. The ability to control tension is extremely important to the surgeon regardless of the type of surgical procedure being performed.

However, during endoscopic surgery, knotting of the suture material is time consuming and burdensome due to the difficult maneuvers and manipulation which are required through the small endoscopic openings.

Many attempts have been made to provide devices to overcome the disadvantages of conventional suturing. Such prior art devices have essentially been staples, clips, clamps or other fasteners. However, none of these above listed devices overcome the disadvantages associated with suturing bodily tissue during endoscopic surgery.

Accordingly, there is a need for improvements in suturing devices which overcome the shortcomings and drawbacks of prior art apparatus.

SUMMARY

The present disclosure relates to handle assemblies for endoscopic suturing and/or stitching devices or the like.

According to an aspect of the present disclosure, a handle assembly for operating an articulatable surgical instrument is provided and includes a housing; an actuation shaft translatably and rotatably supported in the housing; a first trigger supported on the housing and connected to the actuation shaft, the first trigger being configured to translate the actuation shaft to operate a first function of the surgical instrument; a second trigger supported on the housing and connected to the actuation shaft, the second trigger being configured to rotate the actuation shaft to operate a second function of the surgical instrument; and a second-trigger release supported in the housing, the second-trigger release having a first position blocking actuation of the second trigger and a second position permitting actuation of the second trigger, where the second-trigger release is actuated from the first position to the second position upon and complete actuation of the first trigger.

DETAILED DESCRIPTION OF THE DRAWINGS

The foregoing objects, features and advantages of the disclosure will become more apparent from a reading of the following description in connection with the accompanying drawings, in which.

DETAILED DESCRIPTION OF EMBODIMENTS

Figure 1:
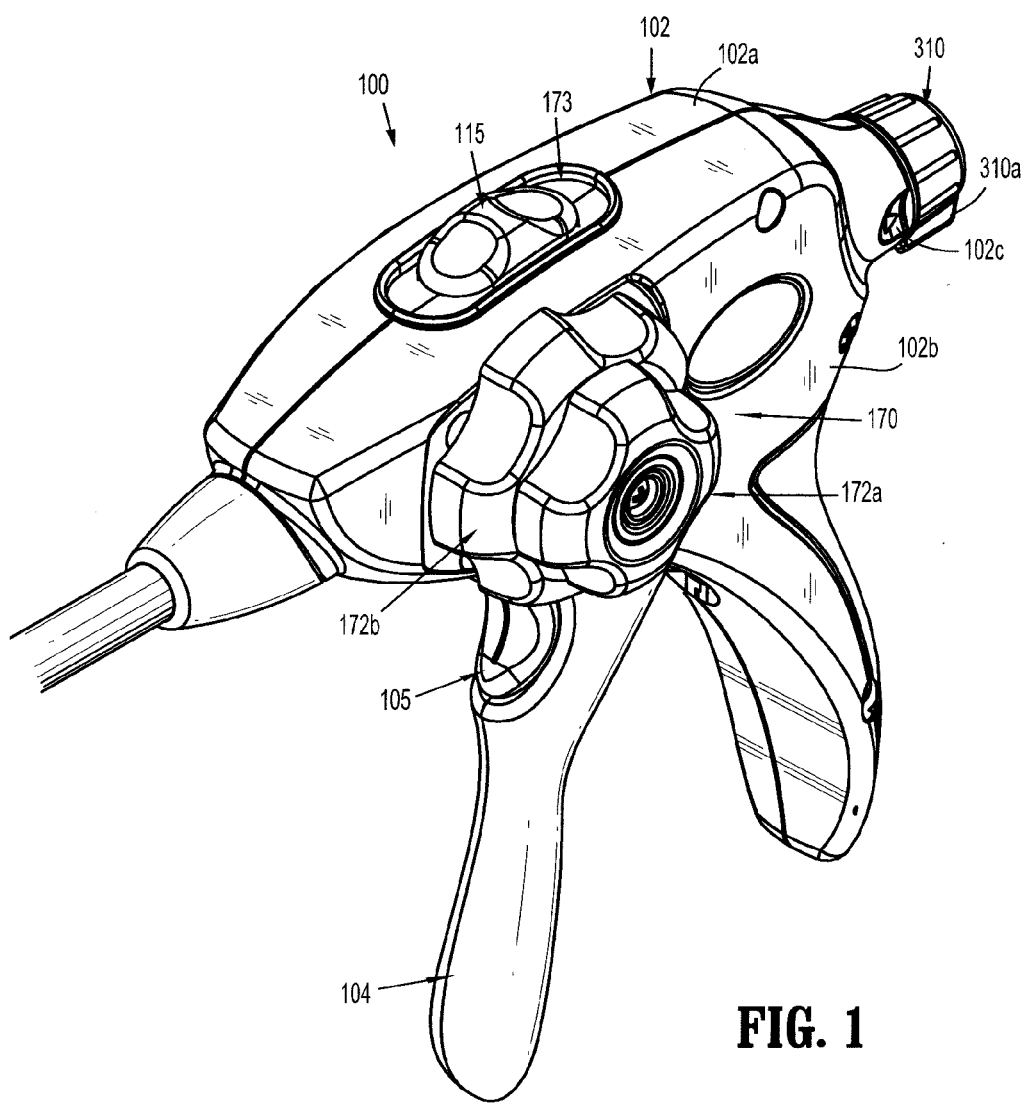
FIG. 1 is a front perspective view of a handle assembly, for an endoscopic suturing device, according to an embodiment of the present disclosure.
Figure 2:
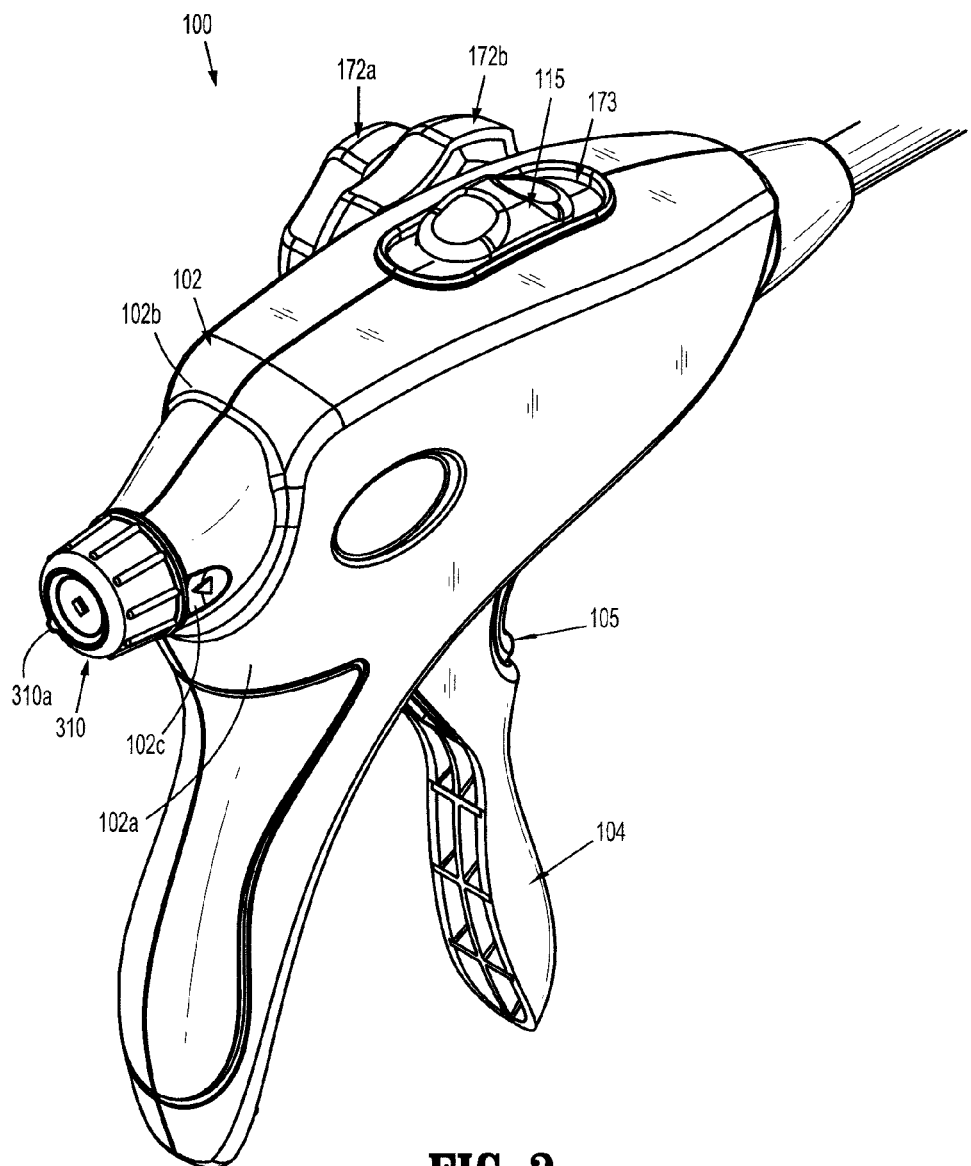
FIG. 2 is a rear perspective view of the handle assembly of FIG. 1.

The present disclosure relates to devices, systems and methods for endoscopic, laparoscopic, endoluminal, and/or transluminal suturing. In one embodiment, for example, such a device comprises a handle, handle assembly or other suitable actuating mechanism (e.g., robot, etc.) connected to a proximal end of a flexible, elongated body portion. A neck assembly operatively supported on a distal end of the flexible, elongated body portion allows an end effector, operatively supported at a distal end of the neck assembly, to articulate in response to actuation of articulation cables. The end effector includes a suture needle and a pair of jaws. In operation, the suture needle is passed back and forth through tissue from one jaw to the other. The device is adapted to be placed in a lumen of a flexible endoscope and then inserted into a natural orifice of a patient and transited endoluminally through the anatomy of the natural lumen to a treatment site within or outside the natural lumen.

In the drawings and in the description which follow, the term "proximal", as is traditional, will refer to the end of the device which is closest to the operator, while the term "distal" will refer to the end of the device which is furthest from the operator.

Referring now in specific detail to the drawings, in which like reference numbers identify similar or identical elements, FIGS. 1-11 illustrate an embodiment of a handle assembly, for an end effector of a stitching device, shown generally at 100. Exemplary end effectors of stitching devices, for use with handle assembly 100, are shown and described in detail in U.S. patent application Ser. No. 12/442,847, filed on May 4, 2009 (now U.S. Pat. No. 8,292,906), entitled FLEXIBLE ENDOSCOPIC STITCHING DEVICES, the entire content of which is incorporated herein by reference.

As seen in FIGS. 1-11, handle assembly 100 includes a housing 102 having a right-half section 102a and a left-half section 102b joinable to one another by suitable fastening elements (not shown), such as screws. Handle assembly 100 includes a first trigger 104 and a second trigger 105, each operatively supported in/on housing 102 and extending therefrom. As will be described in greater detail below, triggers 104, 105 are independently movable between a first un-actuated position, as seen in FIGS. 1-5, and at least one second actuated position. In use, movement of triggers 104, 105 between the first and second positions results in actuation and/or operation of the end effector (not shown).

Figure 9:
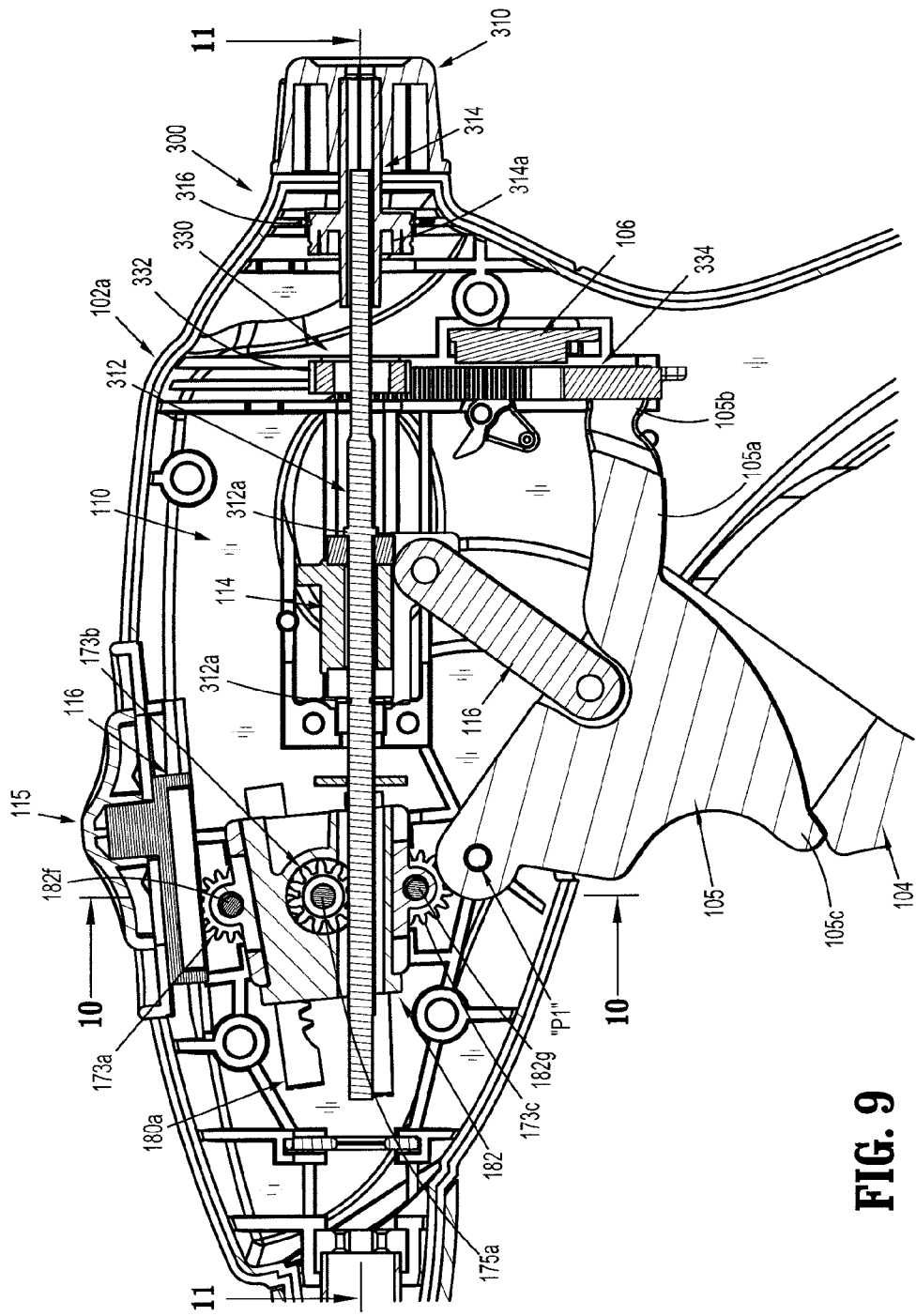
FIG. 9 is a longitudinal, cross-sectional, side elevational view of the handle assembly of FIGS. 1-6, shown in an un-actuated condition.
Figure 9A:
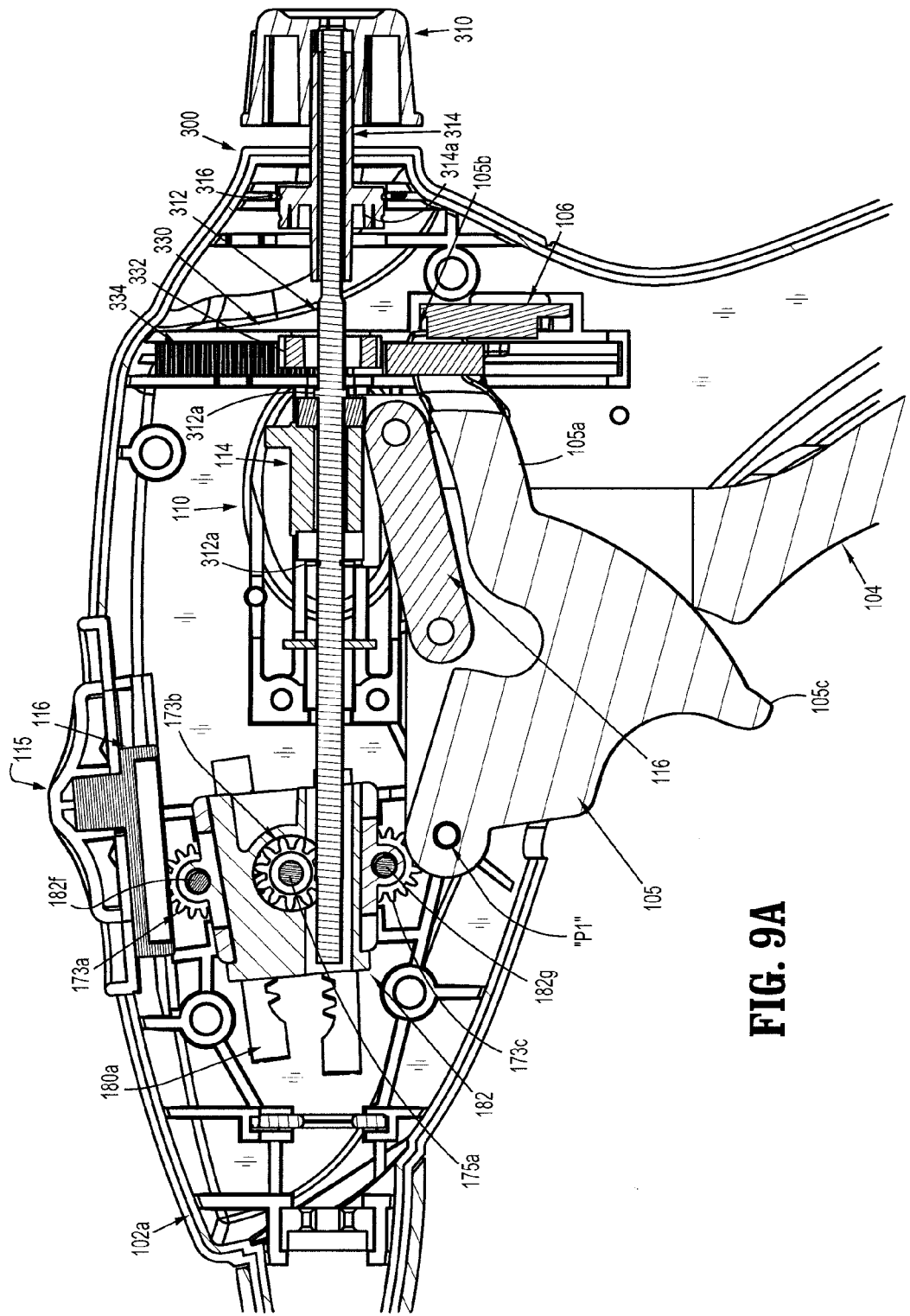
FIG. 9A is a longitudinal, cross-sectional, side elevational view of the handle assembly of FIGS. 1-6, shown in a partially actuated condition.
Figure 10:
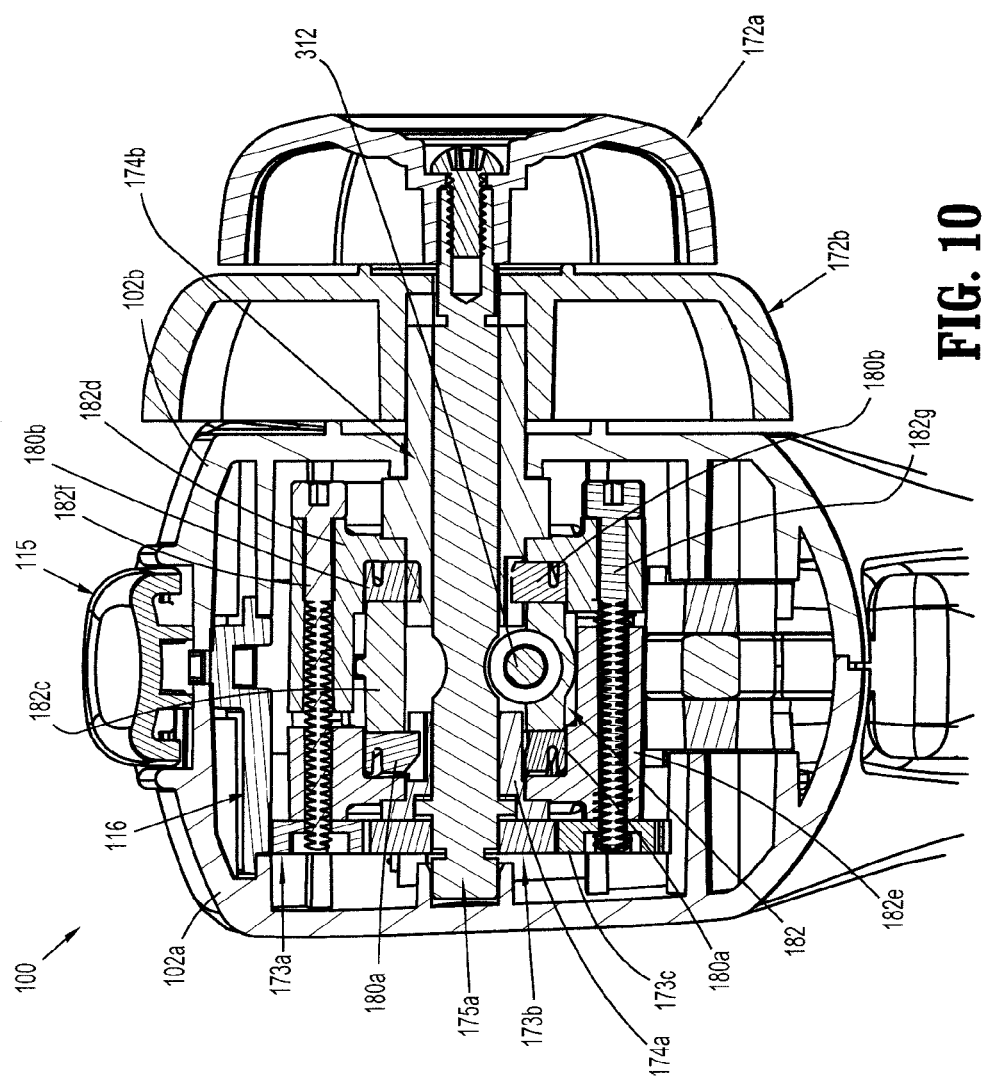
FIG. 10 is a cross-sectional view of the handle assembly of FIG. 9, as taken through 10-10 of FIG. 9.
Figure 11:
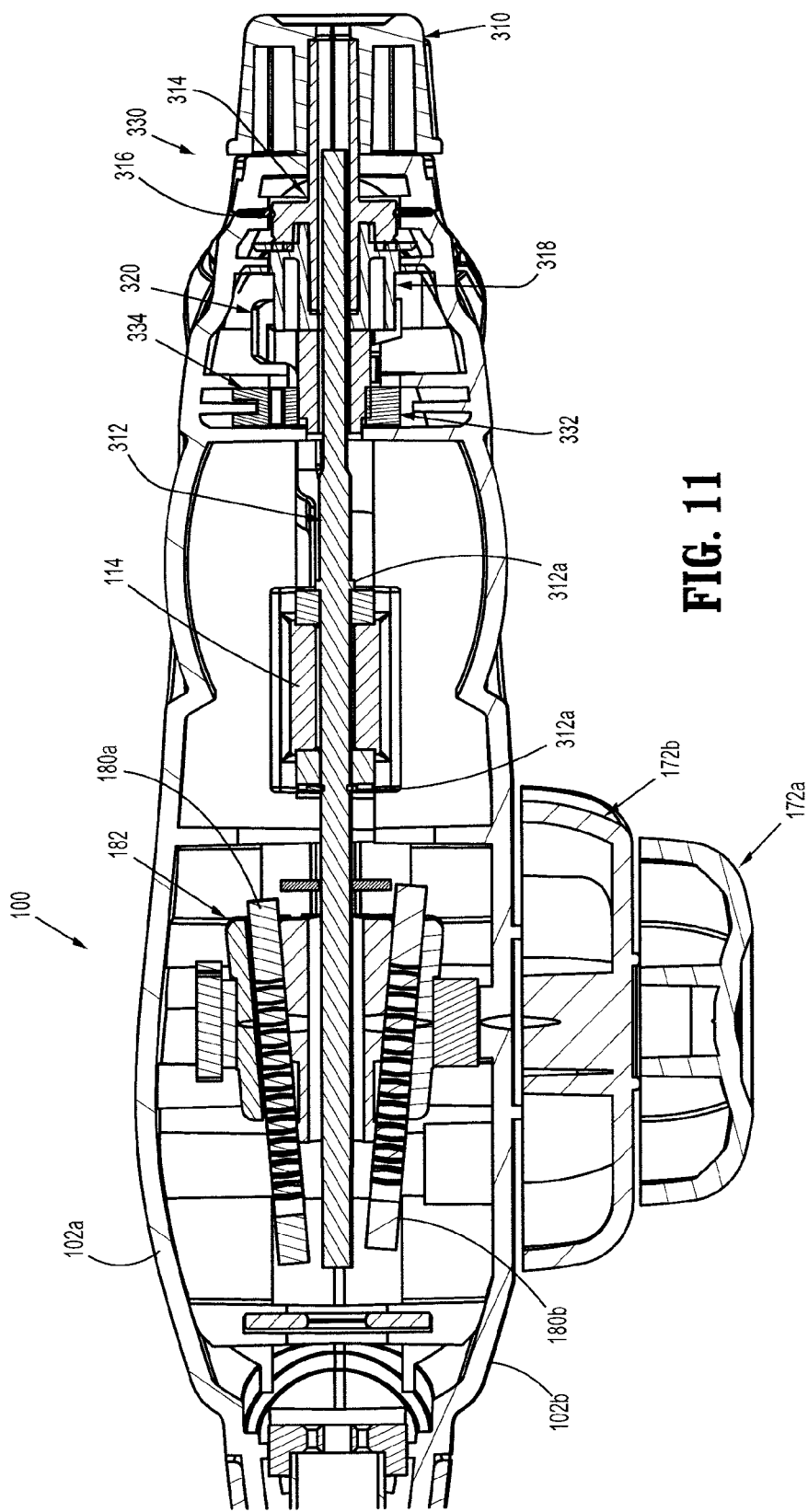
FIG. 11 is a cross-sectional view of the handle assembly of FIG. 9, as taken through 11-11 of FIG. 9.

First trigger 104 is pivotally connected to housing 102 at a pivot point "P1" so as to rotate thereabout. First trigger 104 is operatively associated or otherwise connected to an actuation mechanism 110 (see FIG. 6) of handle assembly 100. In use, movement of first trigger 104 between the first and second positions results in a first function, actuation and/or operation of the end effector. Second trigger 105 is pivotally connected to housing 102 also at pivot point "P1" so as to rotate thereabout. Second trigger 105 is operatively associated or otherwise connected to an actuation mechanism 110 of handle assembly 100. In use, movement of second trigger 105 between the first and second positions results in a second function, actuation and/or operation of the end effector. It is contemplated that second trigger 105 is nested in first trigger and may include a lip 105c (see FIGS. 9 and 9A) configured to engage first trigger 104, when first trigger 104 is moved from an actuated position to an un-actuated position, lip 105c of second trigger 105 is engaged by first trigger 104 thereby also moving second trigger 105 from an actuated position to an un-actuated position.

First trigger 104 may be biased to the un-actuated position by a suitable biasing member, such as, for example a spring or the like (not shown).

First trigger 104 includes a lever arm 104a extending therefrom and into housing 102. A free end of lever arm 104a terminates in a head portion 104b. Lever arm 104a extending from first trigger 104 is formed to have a flattened profile and of a resilient material (e.g., spring steel) in order for lever arm 104a to deflect in a direction transverse to a plane defined by the flattened lever arm. Lever arm 104a of first trigger 104 is curved or biased in a direction out of a plane defined by the plane in which first trigger 104 is actuated.

As seen in FIGS. 3-6, handle assembly 100 further includes a trigger latch 106 supported in housing 102 and located to selectively engage head portion 104b. Trigger latch 106 includes a first cam member 106a projecting toward first trigger 104. First cam member 106a includes a first distal cam surface $106a_1$ configured and oriented to urge or bias head portion 104b of lever arm 104a to a non-biased position as first trigger 104 is moved from the un-actuated position to an actuated position. Trigger latch 106 includes a second cam member 106b projecting toward first trigger 104. Second cam member 106b is spaced a proximal distance from first cam member 106a. Second cam member 106b includes a distal cam surface $106b_1$ oriented in substantially the same direction as first distal cam surface $106a_1$ of cam member 106a. In use, as first trigger 104 is actuated past an initial actuation to a fully actuated position, head portion 104b of lever arm 104a travels from distal cam surface $106b_1$ of cam member 106a to distal cam surface $106b_1$ of second cam member 106b.

Figure 3:
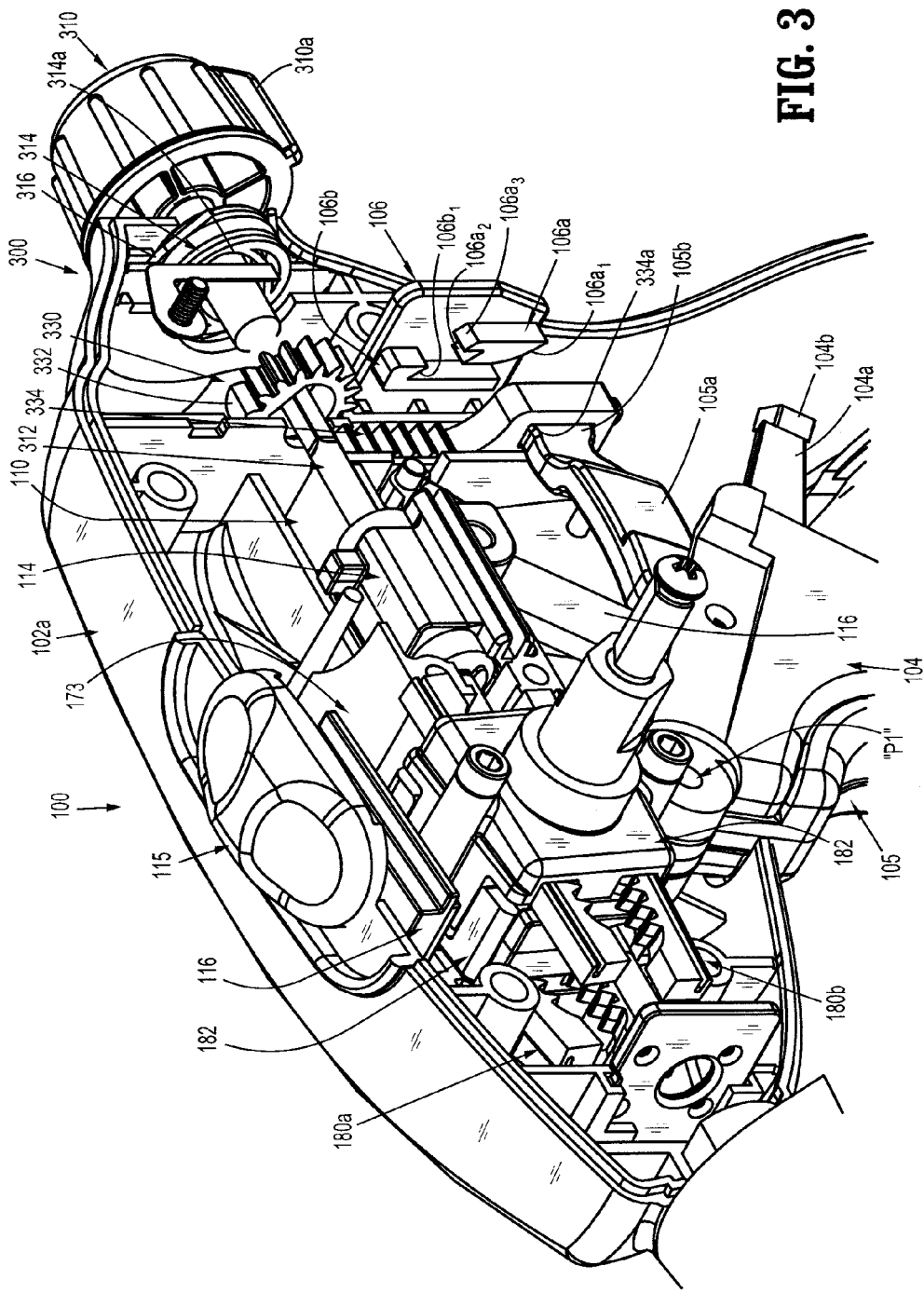
FIG. 3 is a top, front perspective view of the handle assembly of FIGS. 1 and 2, with a housing half-section removed therefrom.
Figure 3A:
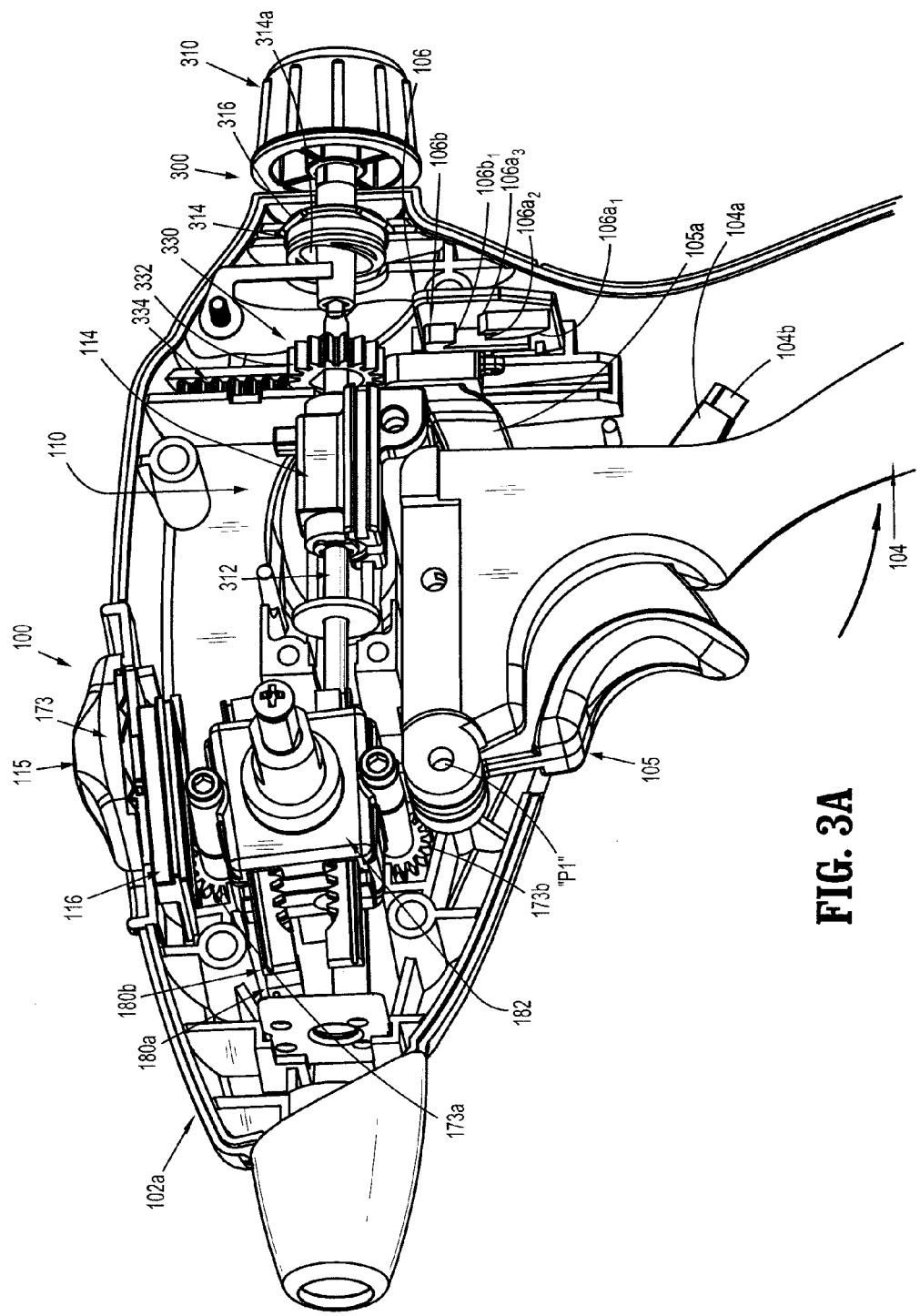
FIG. 3A is a bottom, front perspective view of the handle assembly of FIGS. 1-3, with a housing half-section removed therefrom.

With continued reference to FIG. 3, first cam member 106a includes a proximal notch $106a_2$ formed in a proximal surface of first cam member 106a and spaced an axial distance from distal cam surface $106b_1$ of second cam member 106b. In use, as first trigger 104 is released (i.e., moved in a direction away from the fully actuated position), due to the bias of lever arm 104a, head portion 104b thereof is passed from distal cam surface $106b_1$ of second cam member 106b to notch $106a_2$ formed in a proximal surface of first cam member 106a, thereby stopping first trigger 104 from returning completely to the un-actuated position.

With continued reference to FIG. 3, first cam member 106a further includes a proximal cam surface $106a_3$ formed in a proximal surface of first cam member 106a and located adjacent notch $106a_2$. In use, first trigger 104 is re-actuated, thereby separating or lifting head portion 104b of lever 104 from or out of notch $106a_2$. As head portion 104b of lever 104 is lifted out of notch $106a_2$, the bias of lever 104 moved head portion 104b out of registration with notch $106a_2$ and into registration with proximal cam surface $106a_3$. In this manner, as first trigger is re-released or returned to the un-actuated position, head portion 104b of lever 104 cams against proximal cam surface $106a_3$ and around first cam member 106a.

In this manner, when first trigger 104 is pulled once, upon release thereof, first trigger 104 is held by trigger latch 106 in a partially actuated position. Then, when first trigger 104 is pulled a second time, upon release thereof, first trigger 104 is able to return to the fully un-actuated position.

Second trigger 105 includes a lever arm 105a extending therefrom and into housing 102. A free end of lever arm 105a terminates in a head portion 105b. Head portion 105b of lever arm 105a of second trigger 105 is received in a slot 334a formed in a gear rack 334 of a needle blade actuating assembly 330 (see FIG. 3). Gear rack 334 is slidably supported in housing 102. The structure and function of gear rack 334 will be described in greater detail below.

Handle assembly 100 includes, as seen in FIGS. 3-6, 9 and 9A, an actuation assembly 110 supported in housing 102 and connected to triggers 104, 105. In particular, actuation assembly 110 includes a drive or actuation shaft 312 rotatably and translatably supported in housing 102. Actuation shaft 312 may be rigid and includes a distal end connected to a flexible actuation cable or the like not shown. Actuation assembly 110 includes a drive block 114 axially, translatably supported in housing 102. Actuation block 114 includes a lumen 114a (see FIG. 8) through which actuation shaft 312 passes. Actuation shaft 312 is rotatably disposed within actuation block 114 and is inhibited from axial translation relative to actuation block 114 as a result of any number of stops 312a provided along the length thereof. Exemplary stops 312a include and are not limited to spring clips or ring clamps attached to actuation shaft 312, a flange projecting from actuation shaft 312 and/or the like.

Actuation assembly 110 includes a drive link 116 interconnecting first trigger 104 and actuation block 114. As so configured, as first trigger 104 is actuated from the first un-actuated position to a second actuated position, first trigger 104 acts on drive link 116 which in turn acts on actuation block 114 to urge actuation block 114 in a proximal direction. As actuation block 114 is urged in a proximal direction, actuation block 114 moves actuation shaft 312 in a proximal direction, and in turn the actuation cable is moved in a proximal direction.

Figure 4:
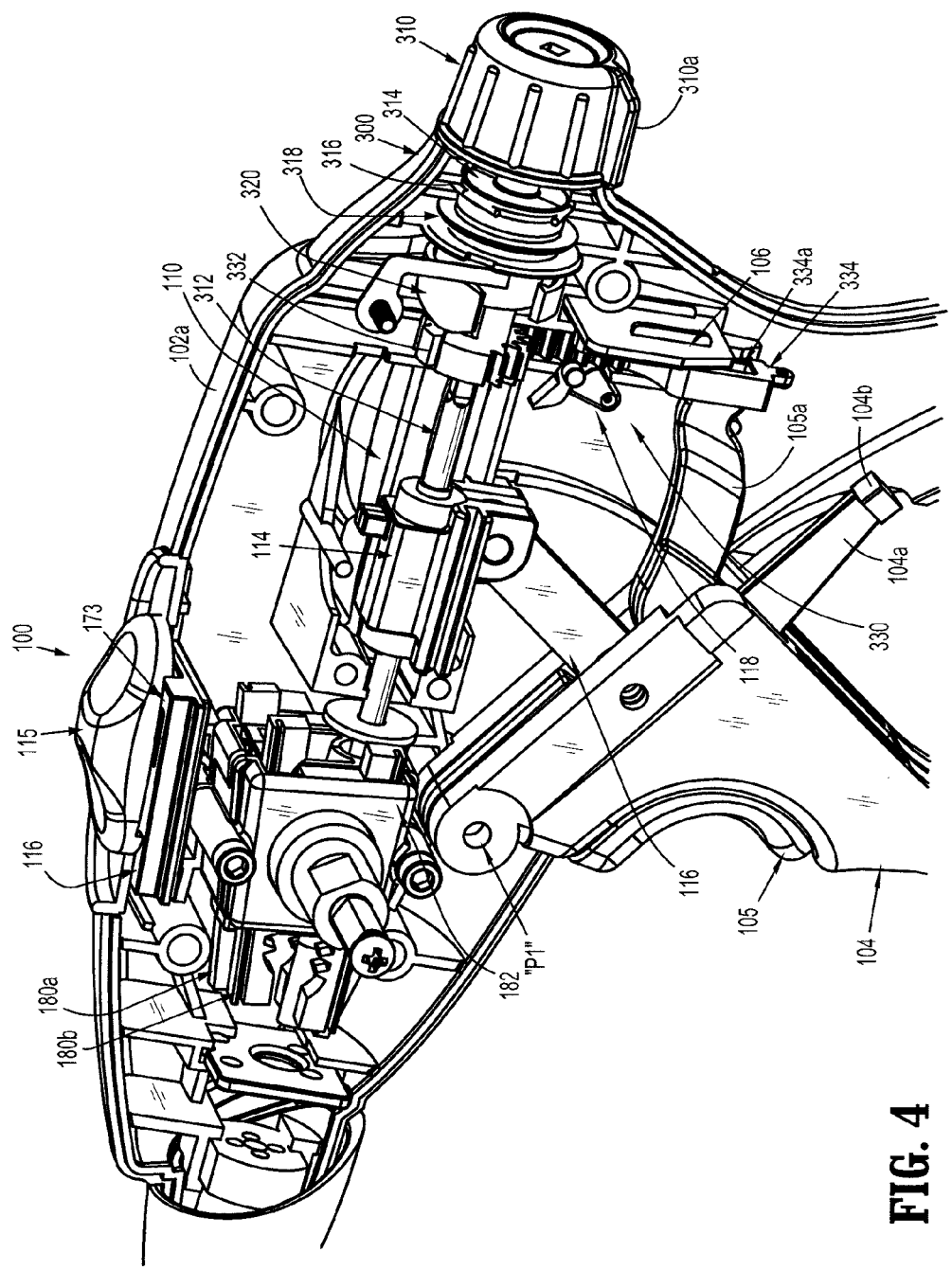
FIG. 4 is a rear perspective view of the handle assembly of FIGS. 1-3, with a housing half-section removed therefrom.
Figures 5, 5A:
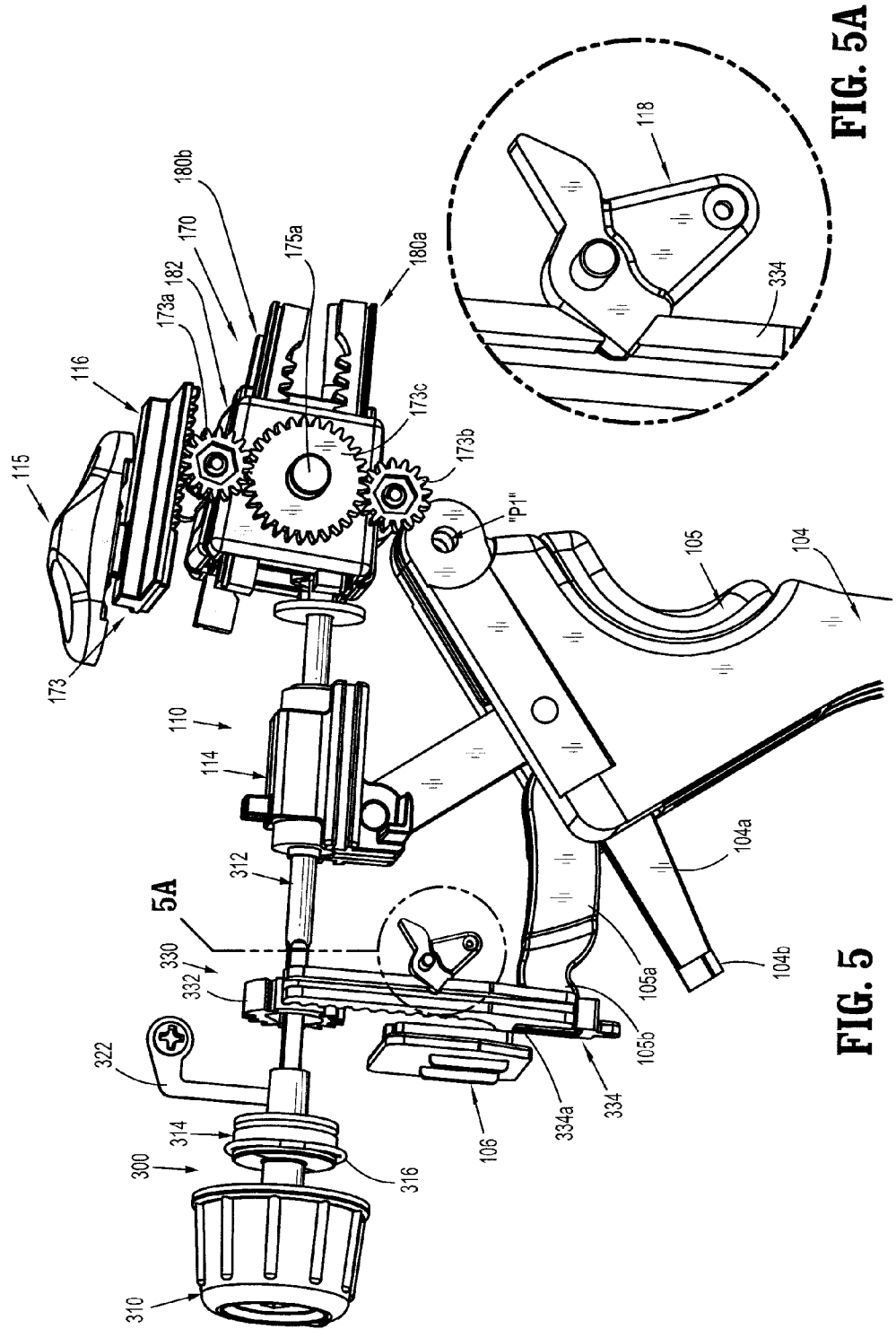
FIG. 5 is a perspective view of the operative components of the handle assembly of FIGS. 1-4, with the housing removed therefrom, shown in an un-actuated condition.
FIG. 5A is an enlarged view of the indicated area of detail of FIG. 5.
Figure 5B:
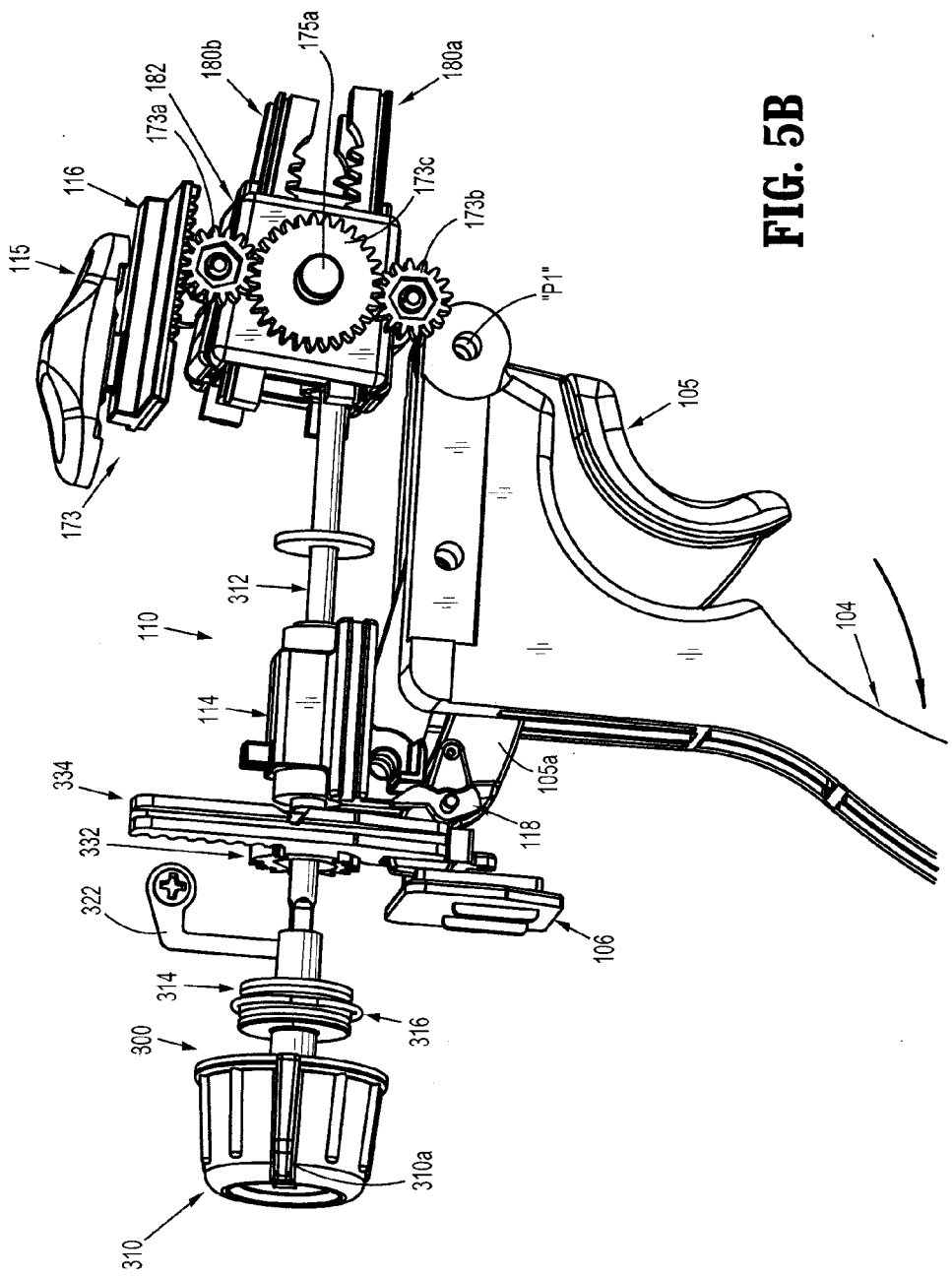
FIG. 5B is a perspective view of the operative components of the handle assembly of FIGS. 1-5A, with the housing removed therefrom, shown in an actuated condition.

As seen in FIGS. 4-5B, actuation assembly 110 further includes a second-trigger release 118 rotatably supported in housing 102. Second-trigger release 118 is biased to a locking condition wherein second-trigger release 118 engages and blocks movement of gear rack 334 of needle blade actuating assembly 330. In use, as first trigger 104 is actuated to move actuation block 114 to the actuated position, actuation block 114 engages second-trigger release 118 to disengage second-trigger release 118 from gear rack 334 of needle blade actuating assembly 330.

Handle assembly 100 includes an articulation assembly 170 supported on and/or in housing 102. Articulation assembly 170 may be operatively connected to the end effector in order to impart multiple articulations to the end effector or any other suitable movement or operation to the end effector.

Figure 6:
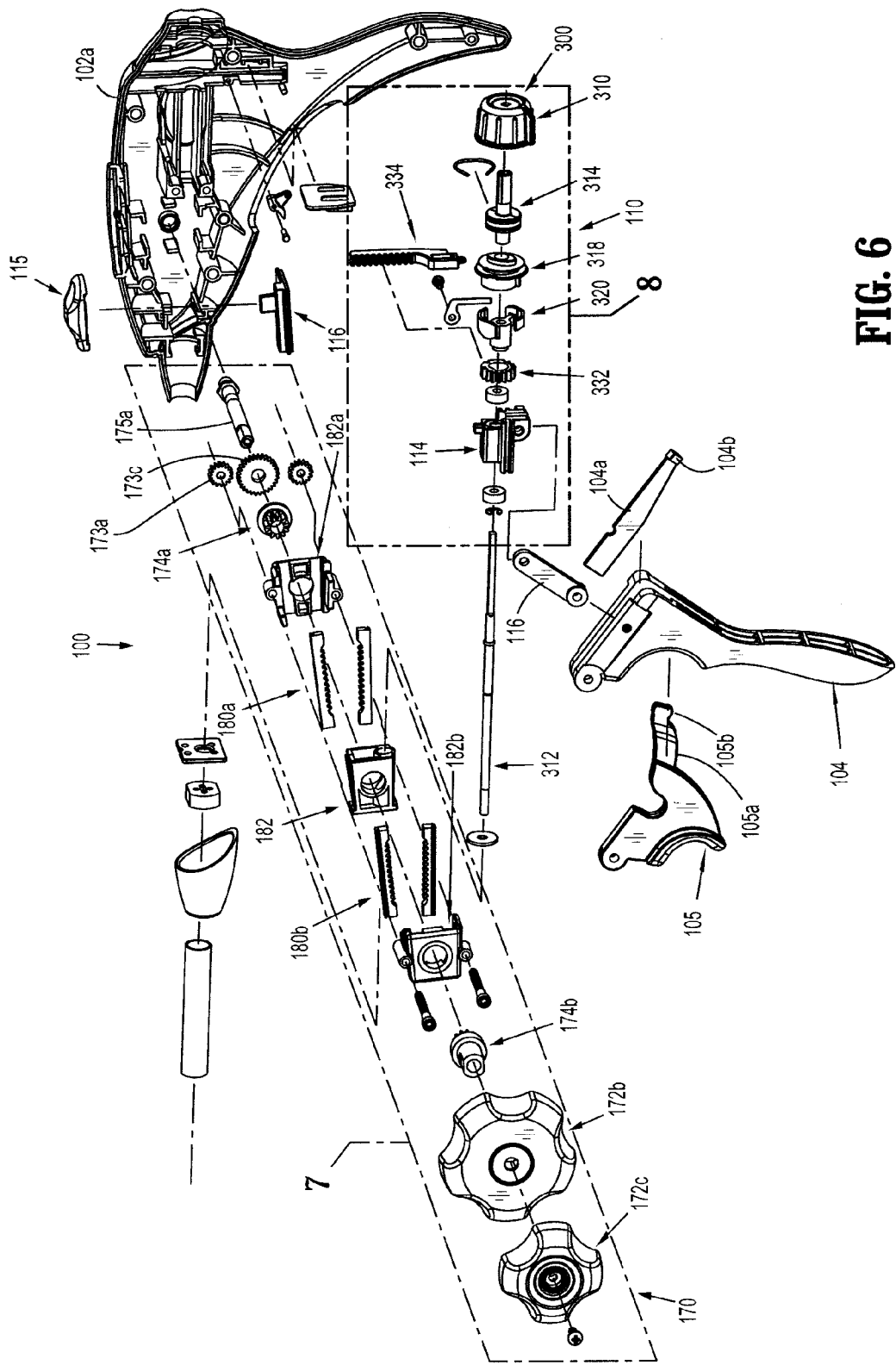
FIG. 6 is an exploded perspective view of the handle assembly of FIGS. 1-5.
Figure 7:
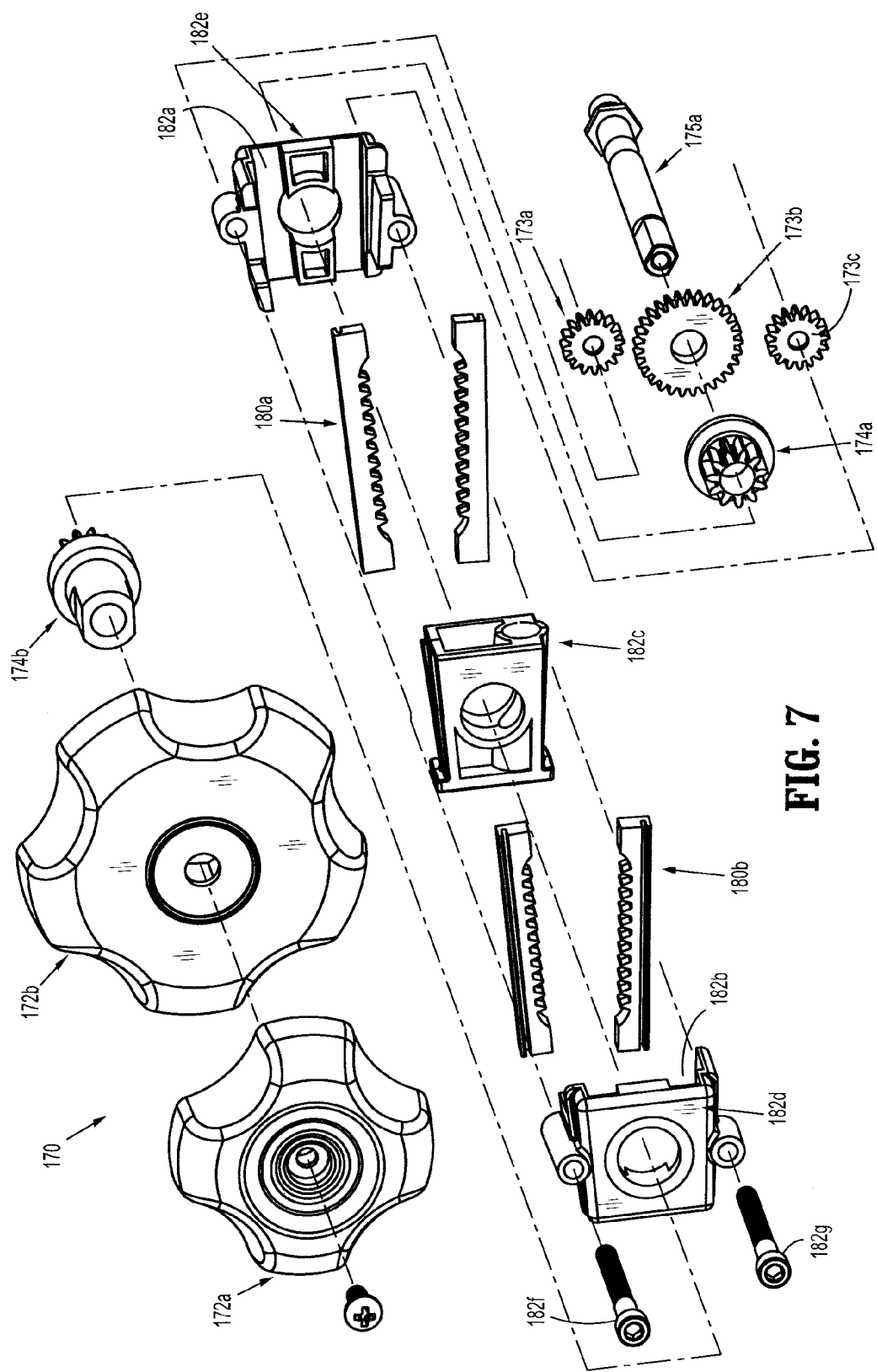
FIG. 7 is an exploded perspective view of an articulation assembly of the handle assembly of FIGS. 1-6.
Figure 8:
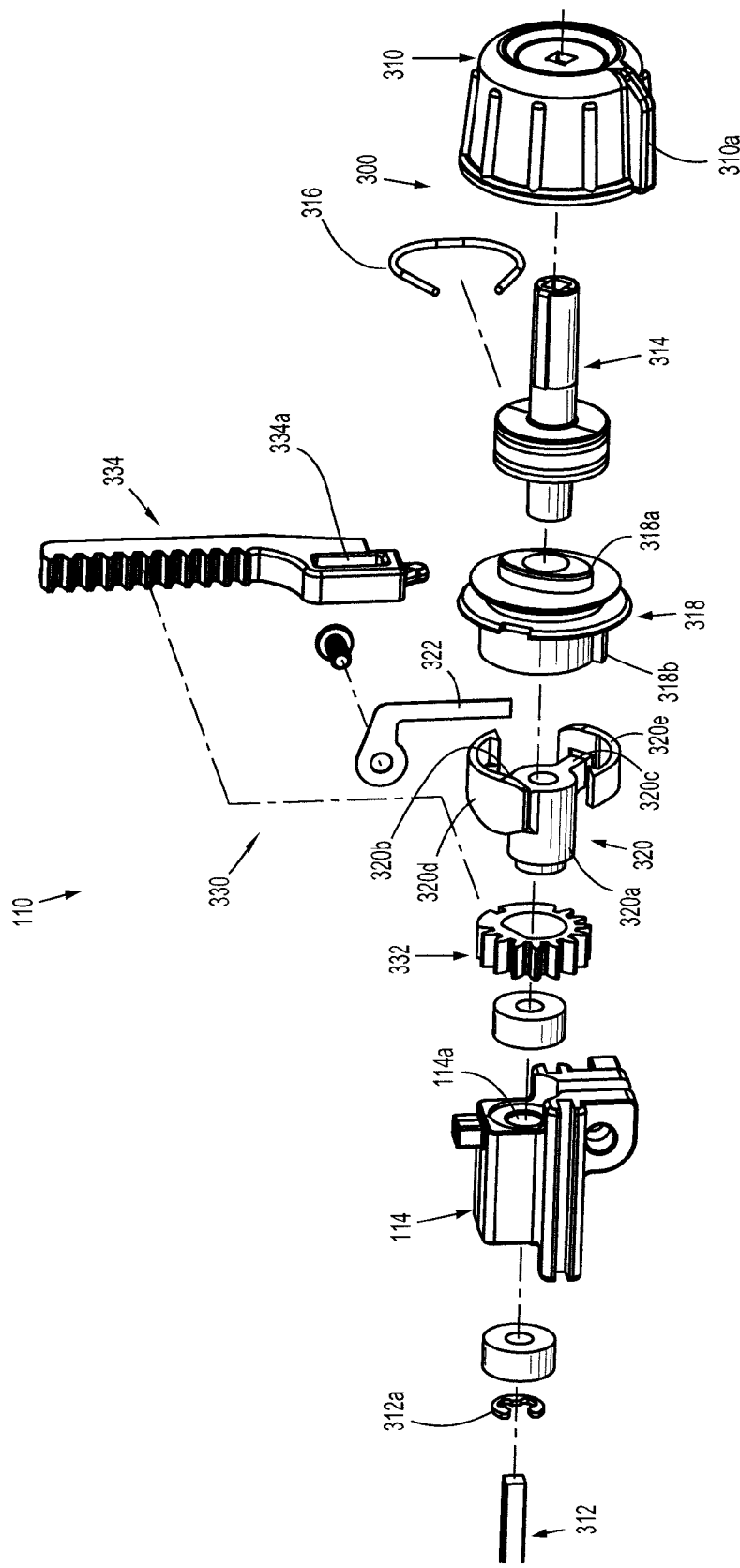
FIG. 8 is an exploded perspective view of a manual needle switching mechanism of the handle assembly of FIGS. 1-6.

As seen in FIGS. 6 and 7, articulation assembly 170 includes a pair of knobs or dials 172a, 172b rotatably supported on or in housing 102, and a set of gears 174 keyed to and sharing a common rotational axis as dials 172a, 172b. The set of gears 174 includes a first gear 174a keyed to first dial 172a, via a rotation shaft 175a, and a second gear 174b keyed to second dial 172b.

Articulation assembly 170 further includes two pairs of opposed racks 180a, 180b with each pair being operatively engaged with and disposed on opposed sides of respective first and second gears 174a, 174b. Each pair of racks 180a, 180b is slidably supported within respective channels 182a, 182b formed in a support member 182. Support member 182 includes a central body portion 182c, and a pair of opposed cap walls 182d, 182e secured to central body portion 182c by suitable screw members 182f, 182g. Screw members 182f, 182g are disposed one each on opposed sides of racks 180a, 180b. Channels 182a, 182b are formed between central body portion 182c and respective cap walls 182d, 182e. In operation, the dimensions (i.e., widths) of channels 182a, 182b may be increased/decreased by adjusting screw members 182f, 182g to either increase/decrease the space between cap walls 182d, 182e and central body portion 182c, and thus increase/decrease friction on racks 180a, 180b.

Each rack of the pair of racks 180a, 180b includes an articulation cable (not shown) secured thereto. In this manner, during operation, as each rack of the pair of racks 180a, 180b is displaced so to is each respective articulation cable.

In operation, as first gear 174a is rotated in a first direction, due to the rotation of first dial 172a and first gear 174a, the first pair of racks 180a are displaced in opposite directions to one another, thus displacing respective articulation cables in opposite directions to one another. It is understood that rotation of first dial 172a in an opposite direction and thus rotation of first gear 174a in an opposite direction will result in movement and/or displacement of the respective pair of racks 180a and articulation cables in opposite directions. Rotation of first dial 172b thus may impart an operation, movement or first articulation of the end effector.

Also, in operation, as second gear 174b is rotated in a first direction, due to the rotation of second dial 172b and second gear 174b, the second pair of racks 180b are displaced in opposite directions to one another, thus displacing respective articulation cables in opposite directions to one another. It is understood that rotation of second dial 172b in an opposite direction and thus rotation of second gear 174b in an opposite direction will result in movement and/or displacement of the respective pair of racks 180a and articulation cables in opposite directions. Rotation of second dial 172b thus may impart an operation, movement or second articulation of the end effector.

As seen in FIGS. 1-5A, handle assembly 100 includes friction adjustment assembly 173. Friction adjustment assembly 173 includes a slide switch 115 translatably supported on housing 102, and a gear rack 116 connected to slide switch 115 and movable therewith. Friction adjustment assembly 173 further includes a first gear 173a threadably supported on screw member 182f and in operative engagement with gear rack 116, a second gear 173b threadably supported on screw member 182g, and a reversing gear 173c operatively inter connecting first and second gears 173a, 173b.

In use or operation, as slide switch 115 is actuated in a first direction, gear rack 116 is actuated in a first direction, and first and second gears 173a, 173b are actuated in first direction to tighten screws 182f, 182g and increase the friction on racks 180a, 180b. Also in use or operation, as slide switch 115 is actuated in a second direction, gear rack 116 is actuated in a second direction, and first and second gears 173a, 173b are actuated in second direction to loosen screws 182f, 182g and decrease the friction on racks 180a, 180b.

The friction on racks 180a, 180b may be increased or decreased as needed in order to assist in maintaining an articulated orientation of the end effector or to assist or enable the end effector to be articulated or un-articulated.

As seen in FIGS. 3-5A, 6 and 8-9A, handle assembly 100 further includes a needle loading assembly 300 including a knob 310 rotatably supported on a rear end of housing 102 and configured to enable loading of a surgical needle in the jaws of an end effector (not shown). Knob 310 includes an indicator 310a, for example, in the form of a rib extending from a side edge thereof, for cooperation with an indicator 102c (see FIGS. 1 and 2) formed on housing 102. Indicators 102c and 310a provide the user with an indication of a relative state of handle assembly 100 and/or the surgical device based on the relative position of indicators 102c, 310a to one another.

Knob 310 is coupled to a proximal end of actuation shaft 312, which has been keyed for connection to knob 310, via a keyed rotation hub 314 rotatably and slidably supported in housing 102. Keyed rotation hub 314 has a shaped outer surface for receipt in a complementary shaped recess formed in knob 310 such that rotation of knob 310 results in rotation of keyed rotation hub 314. Keyed rotation hub 314 defines a shaped lumen (not shown) for receipt of a complementary shaped outer surface of keyed shaft 312 such that rotation of knob 310 also results in rotation of keyed shaft 312. Rotation hub 314 is biased to an advanced or distal position by a biasing member 316, in the form of a C-spring or the like. Thus, in use, as knob 310 is pulled in a proximal direction relative to housing 102, rotation hub 314 is also pulled in a proximal direction and biasing member 316 is biased. Upon release of knob 310, biasing member 316 is free to return to an un-biased condition and thus pull rotation hub 314 and knob 310 in a distal direction relative to housing 102.

As seen in FIGS. 4, 6, 8 and 11, needle loading assembly 300 includes a clutch member 318 rotatably supported in housing 102 and selectively connectable to rotation hub 314. Clutch member 318 is rotatably disposed about keyed shaft 312. Clutch member 318 includes a non-circular shaped stem 318a extending proximally therefrom and being configured for selective engagement in a complementary recess 314a (see FIGS. 3, 3A, 9 and 9A) formed in a distal surface of rotation hub 314. Clutch member 318 includes at least one rib 318b formed on an outer surface thereof.

As seen in FIGS. 4, 6, 8 and 11, needle loading assembly 300 further includes a clutch driver 320 rotatably supported in housing 102 and selectively engageable by clutch member 318. Clutch driver 320 a body portion 320a rotatably disposed about keyed shaft 312, and a pair of opposed arms 320b, 320c extending radially therefrom. Clutch driver 320 further includes a cam wall 320d, 320e supported on a respective end of arms 320b, 320c. Cam walls 320d, 320e are spaced radially outward by an amount sufficient to at least partially surround clutch member 318. Cam walls 320d, 320e are also configured to selectively operatively engage the at least one rib 318b of clutch member 318. In this manner, as clutch member 318 is rotated in a first direction, the at least one rib 318a thereof will engage either cam wall 320d and/or 320e and transmit rotation to clutch driver 320. Also, cam walls 320d, 320e are configured such that rotation of clutch member 318 in a second direction does not result in rotation of clutch driver 320.

Needle loading assembly 300 further includes a spring arm 322, secured to housing 102, and in tangential contact with cam walls 320d, 320e of clutch driver 320. Spring arm 322 is arranged such that a free end thereof will ride over or across cam walls 320d, 320e of clutch driver 320 as cam driver 320 is rotated in the first direction due to the rotation of clutch member 318, and will enter into and between cam walls 320d, 320e of clutch driver 320 as cam driver 320 is rotated in the second direction due to the rotation of clutch member 318 to thereby limit or block rotation of cam driver 320.

As seen in FIGS. 3, 3A, 5, 8, 9 and 9A, handle assembly 100 further includes a needle blade actuating assembly 330 connected to second trigger 105 and to actuation shaft 312. In particular, needle blade actuating assembly 330 includes a spur gear 332 supported on and keyed to body portion 320a of can driver 320. In this manner, rotation of cam driver 320 or spur gear 332 results in rotation of the other of cam driver 320 or spur gear 332. Needle blade actuating assembly 330 further includes a gear rack 334 slidably supported in housing 102, as described above. Gear rack 334 defines a slot 334a for receipt of head portion 105b of lever arm 105a of second trigger 105. Gear rack 334 is positioned in housing 102 such that the gear teeth thereof engage with the gear teeth of spur gear 332.

Accordingly, in use, following actuation of first trigger 104 and the release of gear rack 334 by second-trigger release 118, as described above, as second trigger 105 is actuated from an un-actuated condition, lever arm 105a thereof acts on gear rack 334 to translate gear rack 334. As gear rack 334 is translated the gear teeth thereof cooperate with the gear teeth of spur gear 332 and thus cause spur gear 332 to rotate. As spur gear 332 is rotated, cam driver 320 is also rotated due to spur gear 332 being keyed thereto. As described above, rotation of cam driver 320 in one direction transmits rotation to clutch member 318, on to rotation hub 314 and then to actuation shaft 312. Meanwhile, rotation of cam driver 320 in an opposite direction is limited or blocked by spring arm 322.

As can be appreciated, a distal end of keyed shaft 312 is fixedly secured to a proximal end of an actuation shaft (not shown), and a distal end of the actuation shaft may be connected to an actuation cable (not shown) extending in and connected to the end effectors.

In use, in order to load a surgical needle into jaws of an end effector, knob 310 is pulled in a proximal direction relative to housing 102 (to disengage rotation hub 314 from clutch member 318) and then rotated, thereby rotating keyed shaft 312, the actuation shaft, and the actuation cable. As knob 310 is rotated, blades that are translatably supported in the jaws of the end effector are translated axially until the distal ends of the blades are out of registration with needle receiving recesses formed in the jaws, as evidenced by the alignment of indicator 310a of knob 310 and indicator 102c of housing 102. With the distal ends of the blades out of registration with the needle receiving recesses of the jaws, a surgical needle is inserted into one of the receiving recesses. Knob 310 is then rotated until the distal end of one of the blades engages the surgical needle to hold the surgical needle in the jaw.

While the disclosure has been particularly shown and described with reference to particular embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A handle assembly for operating a surgical instrument, the handle assembly comprising:
   a housing;
   an actuation shaft translatably and rotatably supported in the housing, the actuation shaft defining a longitudinal axis;
   an articulation assembly supported on the housing for effectuating an articulation of an end effector operatively connected to the housing, the articulation assembly being operable to effect articulation of the end effector in a first pair of opposed directions and a second pair of opposed directions which is substantially transverse to the first pair of opposed directions;
   a first trigger supported on the housing and connected to the actuation shaft, the first trigger translating the actuation shaft, upon an actuation of the first trigger, to operate a first function of the surgical instrument;
   a second trigger supported on the housing and connected to the actuation shaft, the second trigger rotating the actuation shaft about the longitudinal axis thereof, upon an actuation of the second trigger, to operate a second function of the surgical instrument; and
   a second-trigger release supported in the housing, the second-trigger release having a first position blocking actuation of the second trigger and a second position permitting actuation of the second trigger, where the second-trigger release is actuated from the first position to the second position upon complete actuation of the first trigger.

2. The handle assembly according to claim 1, wherein the articulation assembly includes a pair of control elements supported on the housing, wherein each control element is operatively connected to a pair of articulation racks.

3. The handle assembly according to claim 2, wherein a first movement of a first of the control elements results in translation of the respective pair of articulation racks in opposed directions to one another, and wherein a second movement of the first of the control elements results in a reversed translation of the respective pair of articulation racks.

4. The handle assembly according to claim 3, wherein a first movement of a second of the control elements results in translation of the respective pair of articulation racks in opposed directions to one another, and wherein a second movement of the second of the control elements results in a reversed translation of the respective pair of articulation racks.

5. The handle assembly according to claim 2, wherein the articulation assembly includes a friction adjustment assembly for increasing/decreasing a friction on each pair of articulation racks.

6. The handle assembly according to claim 5, wherein the articulation assembly includes a support member defining channels configured to slidably support each pair of articulation racks, and wherein the friction adjustment assembly is configured to vary a dimension of the channels of the support member in order to increase/decrease the friction on each pair of articulation racks.

7. The handle assembly according to claim 1, further comprising a trigger latch supported in the housing, the trigger latch being configured for selective engagement by the first trigger upon a first actuation of the first trigger and for disengagement by the first trigger upon a second actuation of the first trigger.

8. The handle assembly according to claim 7, wherein the first trigger includes a resilient lever arm extending therefrom and having a curved profile, and wherein the trigger latch includes cam surfaces against which an end of the lever arm will act during the actuation of the first trigger.

9. The handle assembly according to claim 1, wherein the second trigger is connected to a gear rack, wherein actuation of the second trigger results in translation of the gear rack, and wherein the gear rack engages a spur gear operatively supported on the actuation shaft such that translation of the gear rack results in rotation of the spur gear and rotation of the actuation shaft.

10. The handle assembly according to claim 1, further comprising a drive block translatably supported in the housing, wherein the actuation shaft is axially fixed relative to the drive block such that upon a complete actuation of the first trigger, the drive block is moved proximally with proximal movement of the actuation shaft into engagement with the second-trigger release to move the second-trigger release from the first position to the second position.

11. A handle assembly for operating a surgical instrument, the handle assembly comprising:
    a housing;
    an actuation shaft translatably and rotatably supported in the housing, the actuation shaft defining a longitudinal axis;
    a first trigger supported on the housing and connected to the actuation shaft, the first trigger translating the actuation shaft, upon an actuation of the first trigger, to operate a first function of the surgical instrument;
    a second trigger supported on the housing and connected to the actuation shaft, the second trigger rotating the actuation shaft about the longitudinal axis thereof, upon an actuation of the second trigger, to operate a second function of the surgical instrument; and
    an articulation assembly supported on the housing for effectuating an articulation of an end effector operatively connected to the housing, the articulation assembly being operable to effect articulation of the end effector in a first pair of opposed directions and a second pair of opposed directions which is substantially transverse to the first pair of opposed directions.

12. The handle assembly according to claim 11, wherein the articulation assembly includes a pair of control elements supported on the housing, wherein each control element is operatively connected to a pair of articulation racks.

13. The handle assembly according to claim 12, wherein a first movement of a first of the control elements results in translation of the respective pair of articulation racks in opposed directions to one another, and wherein a second movement of the first of the control elements results in a reversed translation of the respective pair of articulation racks.

14. The handle assembly according to claim 13, wherein a first movement of a second of the control elements results in translation of the respective pair of articulation racks in opposed directions to one another, and wherein a second movement of the second of the control elements results in a reversed translation of the respective pair of articulation racks.

15. The handle assembly according to claim 12, wherein the articulation assembly includes a friction adjustment assembly for increasing/decreasing a friction on each pair of articulation racks; and wherein the articulation assembly includes a support member defining channels configured to slidably support each pair of articulation racks, and wherein the friction adjustment assembly is configured to vary a dimension of the channels of the support member in order to increase/decrease the friction on each pair of articulation racks.

16. The handle assembly according to claim 11, further comprising a trigger latch supported in the housing, the trigger latch being configured for selective engagement by the first trigger upon a first actuation of the first trigger and for disengagement by the first trigger upon a second actuation of the first trigger.

17. The handle assembly according to claim 16, wherein the first trigger includes a resilient lever arm extending therefrom and having a curved profile, and wherein the trigger latch includes cam surfaces against which an end of the lever arm will act during the actuation of the first trigger.

18. The handle assembly according to claim 11, wherein the second trigger is connected to a gear rack, wherein actuation of the second trigger results in translation of the gear rack, and wherein the gear rack engages a spur gear operatively supported on the actuation shafts such that translation of the gear rack results in rotation of the spur gear and of the actuation shaft.

19. A handle assembly for operating a surgical instrument, the handle assembly comprising:
a housing;
an actuation shaft translatably and rotatably supported in the housing, the actuation shaft defining a longitudinal axis;
a first trigger supported on the housing and connected to the actuation shaft, the first trigger translating the actuation shaft, upon an actuation of the first trigger, to operate a first function of the surgical instrument;
a second trigger supported on the housing and connected to the actuation shaft, the second trigger rotating the actuation shaft about the longitudinal axis thereof, upon an actuation of the second trigger, to operate a second function of the surgical instrument;
a second-trigger release supported in the housing, the second-trigger release having a first position blocking actuation of the second trigger and a second position permitting actuation of the second trigger, where the second-trigger release is actuated from the first position to the second position upon complete actuation of the first trigger; and
a drive block translatably supported in the housing, wherein the actuation shaft is axially fixed relative to the drive block such that upon a complete actuation of the first trigger, the drive block is moved proximally with proximal movement of the actuation shaft into engagement with the second-trigger release to move the second-trigger release from the first position to the second position.

\* \* \* \* \*